United States Patent [19]

Evans

[11] Patent Number: 5,419,321

[45] Date of Patent: May 30, 1995

[54] NON-INVASIVE MEDICAL SENSOR

[75] Inventor: Peter D. Evans, Cardiff, United Kingdom

[73] Assignee: Johnson & Johnson Professional Products Limited, Bracknell, United Kingdom

[21] Appl. No.: 316,065

[22] Filed: Sep. 30, 1994

Related U.S. Application Data

[63] Continuation of Ser. No. 952,858, Nov. 16, 1992, abandoned.

[30] Foreign Application Priority Data

May 17, 1990 [GB] United Kingdom ............... 9011131

[51] Int. Cl.$^6$ .............................................. A61B 5/00
[52] U.S. Cl. ....................... 128/633; 128/664
[58] Field of Search ................. 128/633, 664–667; 356/39–41

[56] References Cited

U.S. PATENT DOCUMENTS

| | | |
|---|---|---|
| 3,638,640 | 2/1972 | Shaw . |
| 4,223,680 | 9/1980 | Jobsis . |
| 4,281,931 | 8/1981 | Chikama . |
| 4,321,930 | 3/1982 | Jobsis et al. . |
| 4,485,820 | 12/1984 | Flower . |
| 4,570,638 | 2/1986 | Stoddart et al. . |
| 4,765,340 | 8/1988 | Sakai et al. . |
| 4,889,116 | 12/1989 | Taube . |
| 4,914,512 | 4/1990 | Sekiguchi . |
| 5,057,695 | 10/1991 | Hirao et al. . |
| 5,090,415 | 2/1992 | Yamashita et al. .......... 128/665 |
| 5,139,025 | 8/1992 | Lewis et al. . |
| 5,140,989 | 8/1992 | Lewis et al. . |

FOREIGN PATENT DOCUMENTS 0140633 10/1984 European Pat. Off. .
0290279 5/1988 European Pat. Off. .

OTHER PUBLICATIONS

"Fiber optic reflectance spectrophotometry system for in vivo tissue diagnosis" Ono, et al, Applied Optics/vol. 30, No. 1/ 1 Jan. 1991.

"System for long–term measurement of cerebral blood and tissue oxygenation on newborn infants by near infra–red transillumination" Cope et al, 2200 Medical & Biological Engineering & Computing 26 (1988) May, No. 3, Stevenage, Herts., Gr. Britain.

*Primary Examiner*—Angela D. Sykes
*Attorney, Agent, or Firm*—Bliss McGlynn

[57] ABSTRACT

Apparatus 1 for non-invasive quantitative measurement of a substance in living tissue, the apparatus comprising an electromagnetic radiation emitter 5 to contact a patient's skin, tissue or organ 6, first radiation detector 3 spaced from the radiation emitter 5, and which is also to contact the skin, tissue or organ 6, and second radiation detector 2 which is spaced from the radiation emitter 5 by a distance greater than the spacing between the first radiation detector 3 and the radiation emitter 5, and is to contact the skin, tissue or organ 6. Electrical output signals are produced dependent on the intensity of the radiation detected by the radiation detectors and processed to obtain a value for the concentration of the substance in living tissue.

15 Claims, 2 Drawing Sheets

NON-INVASIVE MEDICAL SENSOR

This is a continuation of U.S. patent application Ser. No. 07/952,858, filed Nov. 16, 1992, now abandoned.

BACKGROUND OF THE INVENTION

This invention relates to apparatus for the non-invasive quantitative measurement of a substance in a human or animal body, and in particular to apparatus for such measurement utilising electromagnetic radiation.

Whilst apparatus according to the invention may be used in the quantitative measurement of a number of substances in the body it will primarily be described, by way of example, for use in determining a quantitative value for tissue oxygenation.

Adequate oxygenation of tissues of patients in the intensive care unit (ICU) is a fundamental requirement, yet at present there is no routine method of non-invasively monitoring intracellular oxygen in intact tissues. Few technologies exist which have the capability to do this. Non-invasive techniques capable of monitoring oxidative metabolism include Magnetic Resonance Spectroscopy ($^{31}$P MRS); Positron emission tomography (PET); NADH fluorimetry; Somatosensory evoked potentials (CNS only); optical monitoring, e.g. visible spectroscopy, Near Infra Red (NIR) multi-wavelength spectroscopy.

Primary objectives in both adult and neonatal intensive care include prevention of brain injury and maintenance of normal neurological function. Most current monitoring techniques in both of these areas determine oxygenation at sites distant from the brain and do not directly access either cerebral oxygen delivery or oxygen utilisation of the brain.

There is, therefore, a real need for a reliable, safe and continuous method of monitoring the oxygen available at the cellular level for respiration in the brain (and other organs) during critical care situations.

Hypoxia (or hypoxaemia), which is the absence of sufficient oxygen in tissues and blood, is the major cause of anaesthetic-related deaths and is also symptomatic of a number of naturally occurring and technically induced health problems and disorders. Damage resulting from a hypoxic state can occur in a matter of seconds and is often irreversible. Intracellular hypoxia causes diverse physiological responses that depend on the sensitivity of different organ systems to oxygen deprivation.

In normal tissues the continuous delivery of oxygen closely matches the oxidalive metabolic requirements of the tissue. These requirements are determined locally and met primarily by regional increases in blood flow and oxygen extraction. Thus, when functional activity is high, oxygen delivery and extraction increase to keep pace with metabolic demand. Similar responses occur in hypoxia when tissues maintain oxygen uptake by maximising blood flow and oxygen extraction.

At present, systemic measurement of oxygen delivery and uptake are used to draw inferences about the availability of oxygen for intracellular processes. These systemic parameters can be helpful when the total supply of oxygen for the body becomes limited; however, they are unsuitable when various tissues respond and adapt differently to changes in regional oxygenation and metabolism.

Thus, any instrument capable of providing continuous, real time, quantitative information on cerebral oxidative metabolism and haemoglobin oxygenation would have significant advantages over current monitoring capabilities.

Living organisms require a continual import of free energy for three major purposes; the performance of mechanical work in muscle contraction and other cellular movements, the active transport of molecules and ions, and the synthesis of macro-molecules and other biomolecules from simple precursors.

Essentially all of the energy needed for cellular metabolism is provided by glucose. Each molecule of glucose provides the energy to form many molecules of ATP (adenosine triphosphate). This occurs by means of a series of electron transfer reactions in which the hydrogen atoms from the glucose are catalytically combined with the oxygen present in cells, to form water. This process occurs in the mitochondria with the flavoprotein-cytochrome chain of enzymes responsible for the transfer of electrons to oxygen. Each enzyme in the chain is reduced and then re-oxidized as the electron is passed down the line. The enzyme complex, cytochrome c oxidase (abbreviated cyt aa$_3$) is the terminal member of the mitochondrial respiratory chain and catalyses approximately 95% of all oxygen utilisation in the human body. In the parallel process of oxidalive phosphorylation, free energy is conserved in the form of high energy phosphate bonds and stored primarily as ATP and creatinine phosphate. The mechanism is chemiosmotic and involves the transfer of protons across an insulating membrane (the inner membrane that forms the cristae of the mitochondria) the transfer being driven by oxidation in the respiratory chain. (Oxidation is the combination of substance with oxygen, or loss of hydrogen, or loss of electrons; the corresponding reverse processes are called reduction.) Cyt aa$_3$ is, therefore, central to cell metabolism. Cyt aa$_3$ is present in measurable quantities in the cerebral cortex and other tissue.

When oxygen is unavailable to cyt aa$_3$ the enzyme is reduced, the rate of electron transport slows, and oxidative phosphorylation decreases. Therefore, the redox state of cyt aa$_3$ is an important indicator of energy provision during pathologic states characterised by disordered oxygen delivery and utilisation. Thus, an ability to continuously measure and monitor the redox state of this oxygen-utilising enzyme to vivo would provide decisive information on the parameter of oxygen sufficiency in tissue(s) or organ(s) in question.

As is well known, radiation in the near infra-red region, having wavelengths in the range 700–1300 nm, can penetrate soft tissue and bone surrounding a living organ, and the emerging light can be related to oxidative metabolism. In addition, and of significant importance, it is further known that cyt aa$_3$ in living body tissue exhibits an oxygen-dependent absorption band in the 700 to 1300 nm wavelength range.

When this key enzyme in oxidative reactions is in the presence of sufficient oxygen, a weak absorption band exists in the 780 to 870 nm region with a maximum at a wavelength of about 820 to 840 nm. The absence of oxygen results in a complete reduction of the enzyme and the disappearance of the absorption band.

British Patent Specification 2075668 discloses apparatus for providing information regarding the oxygenation of specific tissue or organs (e.g. the brain), by monitoring the absorption by cyt aa$_3$, of NIR radiation having wavelengths in the abovementioned region.

Haemoglobin also absorbs light in the near infra-red region of the spectrum. In addition, haemoglobin absorbs differently depending on whether it is present in its oxygenated form (HbO$_2$) or reduced form (Hb). Thus the optical signals are affected by the amounts of arterial and venous blood in the field of observation. To obtain the cyt aa$_3$ signal it is therefore necessary to determine, and remove, the Hb and HbO$_2$ contributions to light absorption in the NIR, and eliminate their interference with the cyt aa$_3$ signal. To do this multiple monochromatic light sources are required. Such light sources, together with suitable algorithms, enable simultaneous equations to be constructed and solved for the three unknowns (Hb, HbO$_2$, cyt aa$_3$) giving qualitative information about these compounds.

Since three overlapping absorption spectra must be de-convoluted, absorption data are needed for a minimum of three NIR wavelengths to measure contributions by the three molecular species of interest. (Four wavelength algorithms provide more accurate descriptions of NIR absorption and scattering by tissues).

Such apparatus is useful as a trend monitor but quantitative results are unattainable since calibration of the apparatus is not possible for the following reasons:

a) Material such as skin or bone through which the radiation is passing will reduce the radiation intensity both before and after passing through the particular tissue of interest; this will vary from patient to patient.

b) The efficiency with which the incident radiation is guided into the body is unknown and variable, as is the efficiency with which the radiation is transferred from the body to the detector.

c) The path length of the radiation within the tissue under test cannot be accurately determined and can only be estimated by photon time of flight measurements.

As is well known in the art, the path length is critical to the intensity of radiation detected by the detector. This relationship is given by the Beer-Lambert Law.

$$\ln(I_o/I) = d \times E \times c$$

where $\ln = 2.303 \log_{10}$ $I_o$=Intensity of source radiation impinging on the sample I=Intensity of radiation transmitted through the sample E=Absorption (extinction) coefficient of the solute species at the wavelength of the source radiation impinged on the sample d=Optical distance or path length (travel path length of radiation transmitted through sample) c=Concentration of substance being measured.

These uncertainties and variables mean that the use of apparatus of the type described above is not a quantitative technique, that is it cannot be applied from patient to patient without calibrating the instrument for each individual patient.

SUMMARY OF THE INVENTION

According to the invention, there is provided apparatus for non-invasive quantitative measurement of a substance in living tissue, which apparatus comprises:

a) emitter means capable of emitting electromagnetic radiation, said emitter means being arrangeable in use in contact with the skin, tissue or organ of a patient, b) first radiation detection means spaced from said emitter means, and arrangeable in use in contact with the skin, tissue or organ of said patient, c) means for producing a first electrical output signal dependent on the intensity of the radiation detected by said first radiation detection means, d) second radiation detection means spaced from said emitter means by a distance greater than said spacing between said first radiation detection means and said emitter means, and arrangeable in use in contact with the skin, tissue or organ of said patient, e) means for producing a second electrical output signal dependent on the intensity of the radiation detected by said second radiation detection means, and f) means for processing said first and second output signals such that a quantified index of said substance in the body is obtainable.

Advantageously, the apparatus is adapted for continuous and/or discontinuous measurement of said substance such that discrete or continuous measurements can be made.

It is preferred that the emitter means is capable of emitting electromagnetic radiation of a wavelength which the substance under investigation in the body is known to absorb. In one embodiment where the substance under investigation is cyt aa$_3$ and/or Hb, and or HbO$_2$, (the concentrations of which are dependent on tissue oxidative metabolism), it is preferred that the emitter means is capable of emitting electromagnetic radiation of a wavelength between 350 and 1600 nm, and more preferably in the range 700 to 1300 nm.

Advantageously, the emitter means comprises a plurality of independently actuatable sub-emitters. Preferably, at least three sub-emitters are provided, each being advantageously arranged to emit radiation of a discrete wavelength. In a preferred embodiment four sub-emitters are utilised. The radiation sources for the sub-emitters may, for example, be as described in the above-mentioned British Specification 2075668.

It is preferred that at least one of the first and second detection means, more preferably both, are at least part annular detectors. It is particularly preferred that the first and second detection means should be annular detectors arranged concentrically encircling the emitter means.

The radiation detection means and the means for producing the output signal may be combined, for example, as in a photodiode. Alternatively, the means for producing the electrical signal, for example, a photomultiplier, may be remote from the detection means and connected thereto by a light guide such as an internally reflecting waveguide or the like.

In apparatus according to the invention, at least the emitter means and first and second radiation detector means are preferably provided in a single housing unit, for ease and convenience of use.

Preferably, the means for processing the first and second output signals include signal conditioning and amplification means. Advantageously, the apparatus may incorporate means for administering oxygen to the patient, which means is advantageously operable when the processed value for the concentration of the substance (e.g. cyt aa$_3$) obtained falls below a predetermined minimum value.

It is preferred that means is provided for attachment of the apparatus to the skin, tissue or organ of the patient.

Whilst the apparatus according to the invention has been described in relation to determining the concentration of substances in the body which are related to oxidative metabolism, it will be appreciated that this form of apparatus may be used for determining the concentration of a wide range of substances in the body by the use of suitable wavelength electromagnetic radiation sources.

BRIEF DESCRIPTION OF THE DRAWINGS

The invention will now be further described, by way of example only, with reference to the accompanying drawings, in which.

DESCRIPTION OF THE PREFERRED EMBODIMENT(S)

Figure 1:
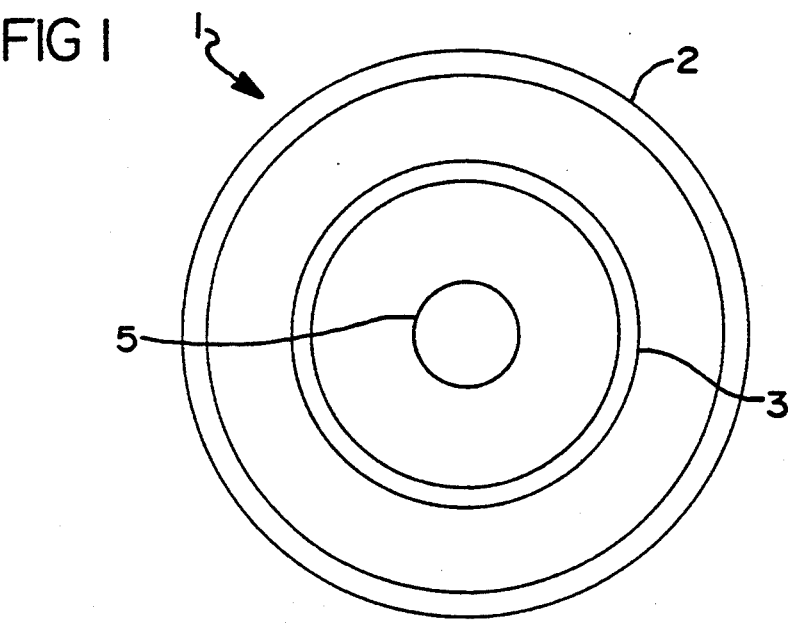
FIG. 1 is a schematic plan view of apparatus according to the invention.
Figure 2:
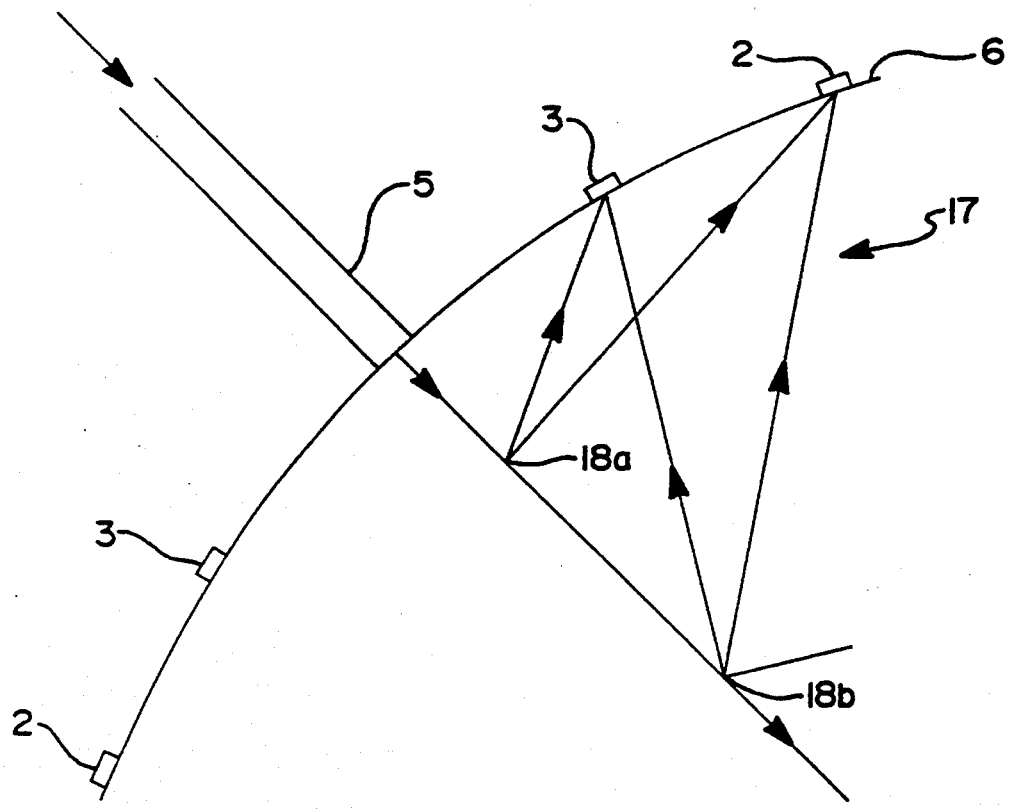
FIG. 2 is a cross-section through the apparatus of FIG. 1 in use.

Referring to FIGS. 1 and 2, a sensor, generally designated 1, consists of a central emitter core 5 carrying light from four sub-emitter laser-diodes each capable of emitting infra-red radiation at a discrete wavelength within the range 700–1300 nm. Arranged concentrically around the core 5 is a primary inner annular photodetector ring 3, and spaced therefrom a secondary outer annular photodetector ring 2. Referring to FIG. 2, the photodetector rings 2, 3 are coupled to respective photomultipliers (not shown), which are in turn connected to respective channels 7, 8 of suitable electronic amplification and signal processing circuitry. The output signals from the photodetector rings 2, 3 are then passed via signal steering circuitry 9 and analogue to digital convertor 12 to a microprocessor control unit 13 programmed to calculate set algorithms dependent on the ratio of the two output signals enabling a value for the relationship between oxygen availability and oxygen consumption at the cellular level to be obtained, which is then recorded or displayed on a VDU and chart recorder 10 and 11. Data can also be stored on computer 16.

Figure 3:
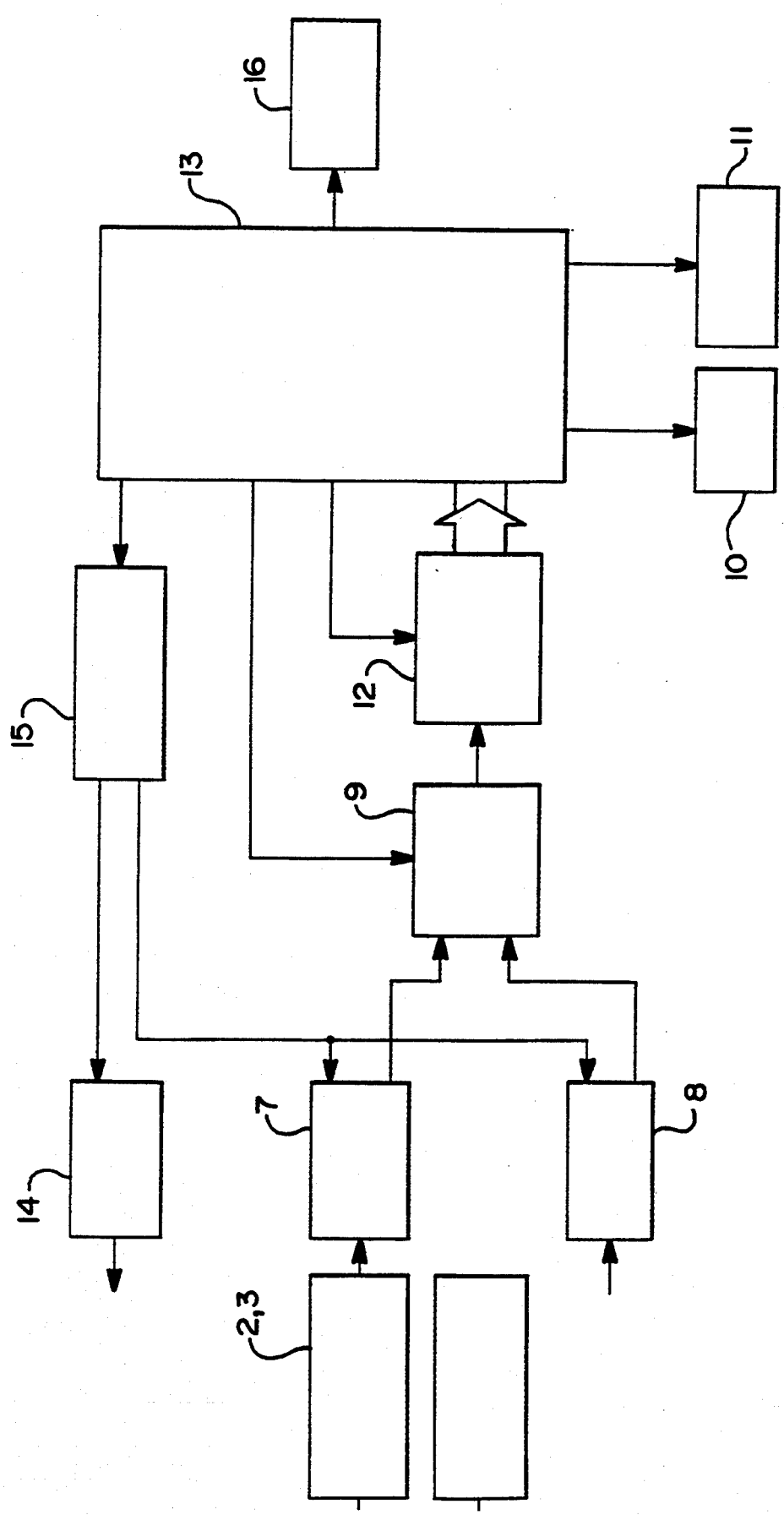
FIG. 3 is a block diagram of a control system used with apparatus according to the invention.

FIG. 3 also shows how the laser power supply drive and firing circuitry, 14 and respective signal processing channels 7, 8 are both controlled by a timing sequence controller 15 connected to the microprocessor control unit 13.

The calibration of the apparatus enables a value for the relationship between oxygen availability and oxygen consumption at the cellular level to be found.

The use of a two detector system enables a reproducible relationship to be established between the path length of the two optical paths used. This relationship will apply from patient to patient, and in this way the Beer-Lambert law can be applied to quantify the substance (in this case e.g. cyt aa3) in the volume of tissue 17 under investigation beneath the sensor.

The assumption is made here that the coupling efficiencies between the body and the two detectors are equivalent and also that the signal attenuation caused by the radiation passing through the regions contiguous with each detector will be equivalent for each detector. This means that the signal attenuation measured between photodetectors 3 and 2 should be due to absorption occurring in the predicted measurement region.

Referring to FIG. 2 in particular, in use the sensor is placed on the tissue surface 6 (e.g. the head) with the annular photodetector rings 2, 3 and emitter core 5 in contact therewith, the radiation (in this case near infrared radiation) enters the tissue and scatters (see arbitrary scattering points 18a, 18b) to follow multiple paths around inside the tissue before being detected by the annular photodetector rings 2, 3. The signal generated at the photodetector rings is then amplified and processed as described above.

The apparatus according to the invention provides further advantages in the following areas:

1. The arrangement of the photodetectors 2, 3 concentrically around the emitter core 5 allows very large area detectors, while still maintaining constant light path lengths to all parts of each detector. This increases the measured signal strength, without compromising path length considerations, and averages out local irregularities in skin pigmentation (e.g. freckles).

2. Due to its unitary construction, positioning of the sensor requires less skill, and has less effect on the results obtained that in the case of the separate emitter-detector arrangement.

3. The reduced sensitivity to the positioning of the sensor should mean that the sensor is less prone to motion artefact, a factor of great importance in any optical system.

I claim:

1. Apparatus for non-invasive monitoring of a substance in living tissue, which apparatus comprises:
   a) emitter means capable of emitting electromagnetic radiation, said emitter means being arrangeable in use in contact with the skin, tissue or an organ of a patient;
   b) first radiation detection means arrangeable in use in contact with the skin, tissue or organ of said patient, said first radiation detection means being spaced from said emitter means to detect radiation which has been scattered and attenuated by the skin, tissue or organ of said patient;
   c) means for producing a first electrical output signal dependent on the intensity of the radiation detected by said first radiation detection means;
   d) second radiation detection means arrangeable in use in contact with the skin, tissue or organ of said patient, said second radiation detection means being spaced farther away from said emitter means than said first radiation detection means and be in a ranged to detect radiation which has been scattered and attenuated by the skin, tissue or organ of said patient;
   e) means for producing a second electrical output signal dependent on the intensity of the radiation detected by said second radiation detection means; and
   f) processor means providing a quantitative measure of said substance in said living tissue, said quantitative measure being dependent on the ratio of said first and second output signals.

2. A method for the non-invasive measurement of a substance in living tissue comprising:
   contacting a patient with said emitter means and said first and second radiation detection means of said apparatus of claim 1;
   emitting electromagnetic radiation through said emitter means into said patient;
   detecting electromagnetic radiation which has been scattered and attenuated by said patient with said first and second radiation detection means; and
   producing a quantitative measure of said substance in said living tissue by determining the ratio of the intensities of said electromagnetic radiation detected by said first and second radiation detection means.

3. The apparatus of claim 1, wherein said first and second radiation detection means are annular and concentrically arranged around said emitter means.

4. The apparatus of claim 1, wherein said emitter means is capable of emitting electromagnetic radiation of a characteristic absorbtion wavelength for said substance.

5. The apparatus of claim 4, wherein said emitter means is capable of emitting electromagnetic radiation of a wavelength between 700 and 1300 nm.

6. The apparatus of claim 1, wherein said emitter means comprises a plurality of independently actuatable subemitters.

7. The apparatus of claim 6, wherein each of said subemitters is arranged to emit radiation of a discrete wavelength.

8. The apparatus of claim 6, wherein there are four said sub-emitters.

9. The apparatus of claim 1, wherein said first detection means and said means for producing said first output signal are combined and said second detection means and said means for producing said second output signal are combined.

10. The apparatus of claim 1, wherein said emitter means and said first and second radiation detection means are provided in a unitary housing.

11. The apparatus of claim 1, including means for administering oxygen to the patient.

12. The apparatus of claim 1, including means for attachment of the apparatus to the skin of the patient.

13. Apparatus for non-invasive monitoring of a substance in living tissue, which apparatus comprises:
   a) emitter means capable of emitting electromagnetic radiation, said emitter means being arrangeable in use in contact with the skin, tissue or organ of a patient;
   b) first radiation detection means arrangeable in use in contact with the skin, tissue or organ of said patient, said first radiation detection means being spaced by a first distance from said emitter means to detect radiation which has been scattered and passed through the patient;
   c) means for producing a first electrical output signal dependent on the intensity of the radiation detected by said first radiation detection means;
   d) second radiation detection means arrangeable in use in contact with the skin, tissue or organ of said patient, said second radiation detection means being spaced by a second distance from said emitter means and by a third distance from said first radiation detection means to detect radiation which has been scattered and passed through the patient, wherein said first distance is at least as great as said third distance;
   e) means for producing a second electrical output signal dependent on the intensity of the radiation detected by said second radiation detection means; and
   f) processor means arranged to provide a quantitative measure of said substance in said living tissue, said quantitative measure being dependent on said first and second output signals.

14. Apparatus according to claim 13, wherein said processor means provides a quantitative measurement of said substance in said living tissue dependent on the ratio of said first and second output signals.

15. Apparatus for non-invasive monitoring of a substance in living tissue comprising:
   a) emitter means capable of emitting electromagnetic radiation, said emitter means being arrangeable in use in contact with the skin, tissue or organ of a patient;
   b) first annular radiation detector means extending around and spaced from said emitter means, and arrangeable in use in contact with the skin, tissue or organ of said patient;
   c) means for producing a first electrical output signal dependent on the intensity of the radiation detected by said first radiation detector means;
   d) second annular radiation detector means arranged concentrically with said first annular radiation detector means, said second annular radiation detector means extending around said emitter means and being spaced from said emitter means by a distance greater than said spacing between said first radiation detector means and said emitter means, said second radiation detector means being arrangeable in use in contact with the skin, tissue or organ of said patient;
   e) means for producing a second electrical output signal dependent on the intensity of the radiation detected by said second radiation detector means; and
   f) signal processor means providing a quantitative measurement of said substance in said living tissue dependent on the ratio of said first and second output signals.

* * * * *

UNITED STATES PATENT AND TRADEMARK OFFICE
CERTIFICATE OF CORRECTION

PATENT NO.   : 5,419,321
DATED        : May 30, 1995
INVENTOR(S)  : Peter D. Evans It is certified that error appears in the above-indentified patent and that said Letters Patent is hereby corrected as shown below:

Column 6, lines 44 and 45, claim 1, "be in a ranged" should be --being arranged--.

Signed and Sealed this

Twenty-third Day of January, 1996

Attest:

BRUCE LEHMAN

*Attesting Officer*   *Commissioner of Patents and Trademarks*